United States Patent [19]

Mizoguchi

[11] Patent Number: 5,262,731
[45] Date of Patent: Nov. 16, 1993

[54] LIQUID LEVEL DETECTOR

[75] Inventor: Fumio Mizoguchi, Tokyo, Japan

[73] Assignee: Olympus Optical Co., Ltd., Tokyo, Japan

[21] Appl. No.: 869,807

[22] Filed: Apr. 16, 1992

[30] Foreign Application Priority Data

Apr. 18, 1991 [JP] Japan .................. 3-86994

[51] Int. Cl.$^5$ .......................... G01N 27/22
[52] U.S. Cl. .................. 324/663; 73/864.24; 340/620
[58] Field of Search .......... 324/663; 340/620; 73/863.01, 864.24

[56] References Cited

U.S. PATENT DOCUMENTS

| 3,635,094 | 1/1972 | Oberli | 73/423 A |
| 4,736,638 | 4/1988 | Okawa et al. | 73/864.24 |
| 4,912,976 | 4/1990 | Labriola, II | 340/620 |
| 4,939,925 | 7/1990 | Sakuma et al. | 73/61.4 |
| 5,012,683 | 5/1991 | Davis | 73/864.24 |
| 5,017,909 | 5/1991 | Goekler | 340/620 |
| 5,049,826 | 9/1991 | Sasao | 73/864.24 |
| 5,083,470 | 1/1992 | Davis et al. | 73/864.24 |

FOREIGN PATENT DOCUMENTS 3001133 7/1989 Fed. Rep. of Germany ...... 340/620
61117460 11/1984 Japan .

Primary Examiner—Kenneth A. Wieder
Assistant Examiner—Christopher M. Tobin
Attorney, Agent, or Firm—Kenyon & Kenyon

[57] ABSTRACT

A test tube holding a liquid specimen therein is arranged between a pair of electrodes arranged in an opposed relation. A conductive nozzle is inserted into a test tube. An oscillator is connected to one of these electrodes and a receiver is connected to the other electrode. A nozzle is connected to a zero potential level common to the oscillator and receiver. When the tip end of the nozzle is brought down into the level of the liquid specimen, there occurs a change in electrostatic capacity between the electrodes and hence a change in the level of a signal transmitted from the oscillator to the receiver. A determining device determines, based on the change in the level of the signal, whether or not the tip end of the nozzle is in contact with the liquid level.

5 Claims, 4 Drawing Sheets

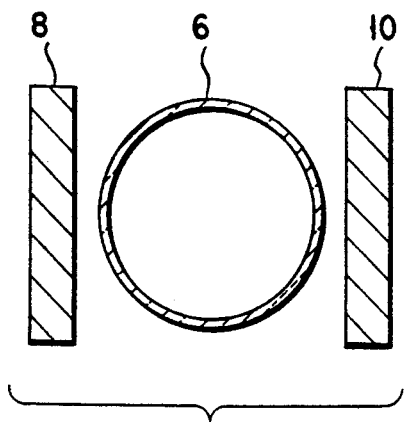
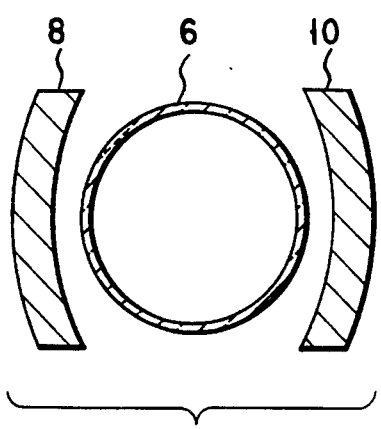
FIG.2A  FIG.2B
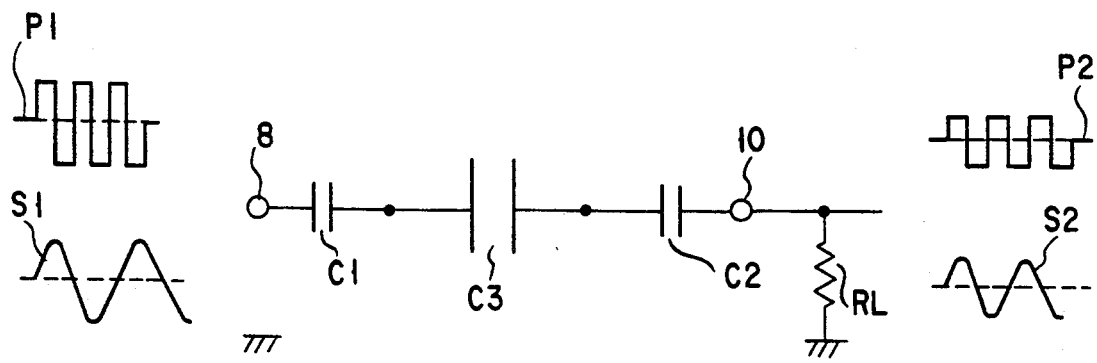
FIG.3A
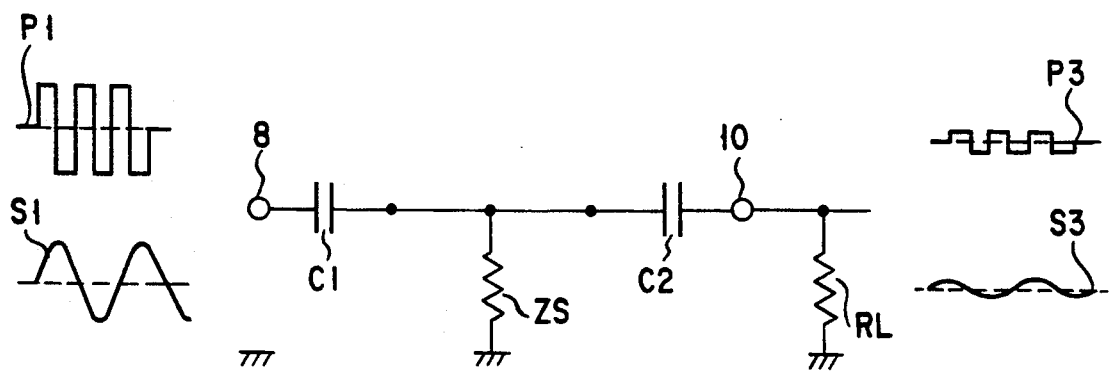
FIG.3B

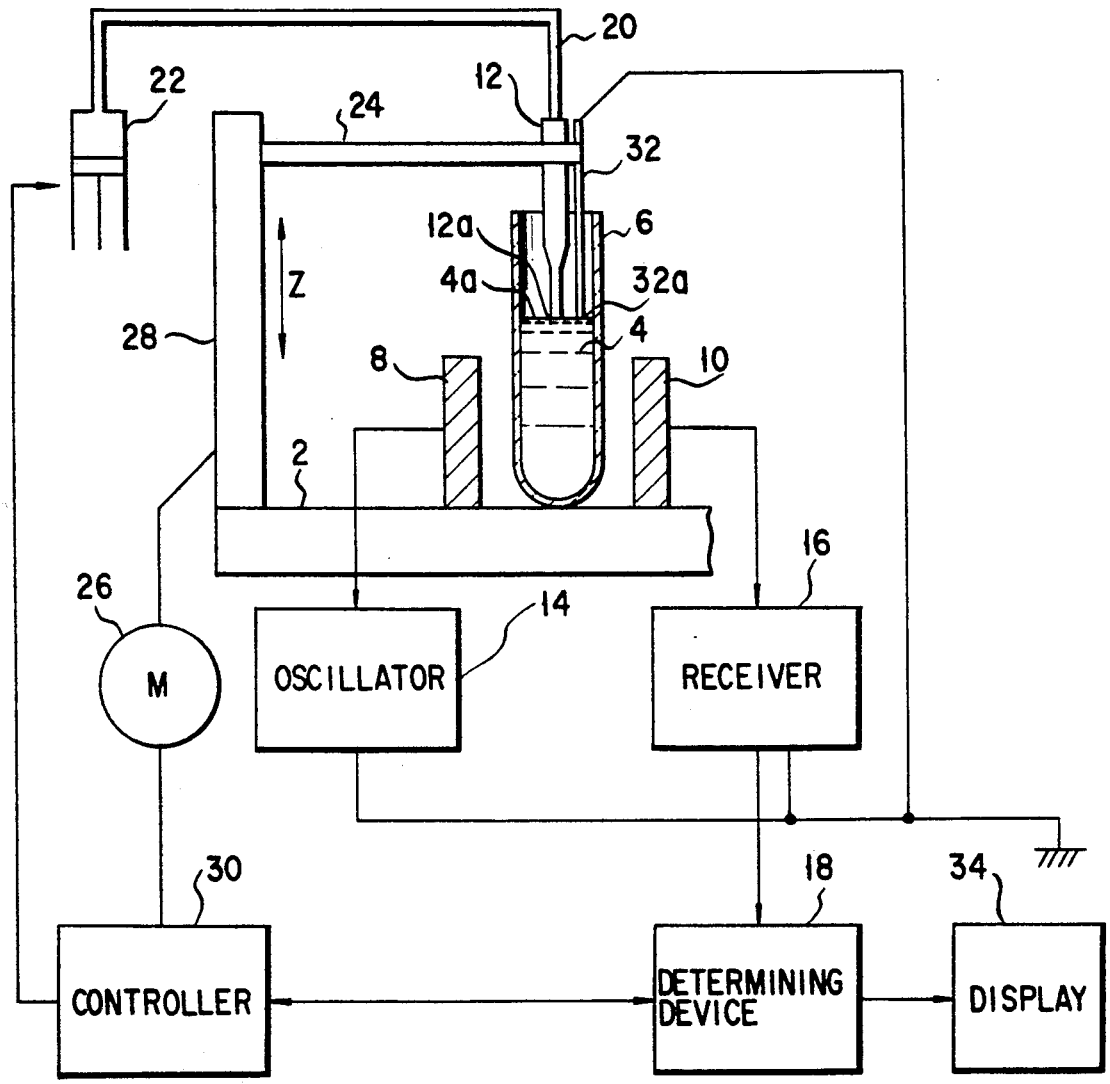
F I G. 4

LIQUID LEVEL DETECTOR

BACKGROUND OF THE INVENTION

1. Field of the Invention

The present invention relates to an apparatus for detecting the level of a liquid specimen, for example, in a test tube or tubes in an automatic analyzer.

2. Description of the Related Art

In an automatic analyzer, a vertically movable mechanism is used for a nozzle for taking up a liquid specimen, such as a blood plasma and corpuscle.

In the case where such a nozzle is employed, it is necessary to detect the contact of the nozzle with the liquid specimen. Unless the contact level can be detected, there is a risk that the nozzle will be immersed too deep or that the descent motion of the nozzle will be mechanically continued on even if a test tube becomes empty. This may cause an adverse effect on the result of analysis of the liquid specimen.

A conventional technique has been developed for detecting the level of a liquid specimen. It is known to detect the level of a liquid through its electrical conductivity. In this method, a pair of electrodes are inserted into a test tube in interlock with an associated nozzle and hence moved vertically down relative to the surface level of the liquid specimen. When the pair of electrodes are brought down to the liquid level, an electric current is carried from one electrode to the other electrode through the conduction of the liquid specimen. It is, therefore, possible to detect the surface level of the liquid specimen by detecting the electrical conduction.

In this method, the electrodes can be mounted integral with a nozzle for liquid level detection, as disclosed in U.S. Pat. No. 4,939,925 and Published Unexamined Japanese Patent Application 61-117460.

Since the test tube is normally narrow in diameter, the nozzle, unless being small-sized, cannot be inserted into the test tube. In particular, a nozzle of synthetic resin is relatively large and improper to insert normally into the test tube.

Forming the electrodes integral with the nozzle can somewhat decrease their occupation area, but the nozzle by itself becomes expensive and is not suitable as a dispensable one.

It is known, as in U.S. Pat. No. 3,635,094, to detect the immersed state of a nozzle in a liquid specimen through the utilization of an electrostatic capacitance involved.

In this method, a test tube or both a support stand and nozzle are made of a conductive material and serves as a pair of electrodes. When the nozzle is immersed in a liquid level, it serves as one electrode against the test tube acting as the other electrode, thus leading to a variation in electrostatic capacitance between the two. The immersion of the nozzle in the liquid specimen can be detected based on a variation in their electrostatic capacitance.

In this detection method, however, there is involved no variation in electrostatic capacitance, unless the nozzle is immersed in the liquid nozzle. In this case it is possible to only detect the fact that the nozzle has been immersed into the liquid specimen. Stated in a stricter sense, this cannot be regarded as a proper detection of the liquid level, offering a detection accuracy problem. Further, the test tube or support stand is restricted principally to a material of high conductivity because the purpose of the material is to enable the test tube or support stand to act as an electrode. Further, the potential on the support stand is held constant so as to provide a reference against the electrode. For this reason, it is not possible to use any inexpensive synthetic resin and glass, resulting in high cost. In the case where the test tube is shifted relative to the support stand, attention should be paid to any defective electrical contact. Thus the positive detection of the liquid level is, therefore, affected.

SUMMARY OF THE INVENTION

It is accordingly an object of this invention to provide a liquid level detector which can accurately detect a liquid level without the need to insert a pair of electrodes into a container and can do so without imparting any restriction to the material of which the container is made.

Accordingly, in its first aspect, this invention provides an apparatus for detecting a level of a liquid held in a container, which comprises:

first and second electrodes arranged with the container set therebetween;

generating means, electrically connected to the first electrode, for generating an electrical signal;

receiving means, electrically connected to the second electrode, for receiving the electrical signal from the generating means through a route of the first electrode, container and second electrode;

a conductive member, electrically connected to a zero potential level common to the generating means and receiving means, vertically movable relative to the level of the liquid; and detecting means for detecting a change of the received electrical signal with respect to a reference electrical signal which is received by the receiving means when the conductive member is not in contact with the liquid level and for determining that the conductive member is in contact with the liquid level, when there is the change of the received electrical signal, so that the liquid level is detected and that the conductive member is not in contact with the liquid level when there is no change of the received electrical signal.

In the liquid level detector, the conductive member is made of, preferably, a conductive synthetic resin.

In order to use an inexpensive nozzle without electrode mounted thereon, the conductive member may be formed as a nozzle for taking up the liquid.

According to a further development of the invention, the liquid level detector further comprises controlling means for controlling a vertical movement of the nozzle relative to the liquid level based on the determination made by detecting means.

According to the liquid level detector described above, an electrostatic capacity is involved in a system in which the container for the liquid specimen is set between the opposed electrodes. In an initial state, that is, in the state where the conductive member is not in contact with the liquid level, a first electrostatic capacity is created between the first electrode and the container and a second electrostatic capacity between the second electrode and the container and a third electrostatic capacity is created in the container. The composite of these electrostatic capacities constitutes an electrostatic capacity in the aforementioned system in that initial state.

In the state in which the conductive member connected to the zero potential level is in contact with the liquid level, the third electrostatic capacity is lost through the conductive member. The amplitude of an electric signal received by the receiving means becomes smaller in that contact state than in the initial state.

Since the electric signal received by the receiving means differs depending upon whether there is the initial state or the contact state, it is possible to determine based on the received signal whether or not the conductive member is in contact with the liquid level.

An advantage of the invention lies in that the liquid level detector is not necessary to insert a pair of electrodes in the container. This ensures the detection of the liquid level even if a relatively narrowed container is used. A container of inexpensive material can be employed because it does not need to be made using a conductive material.

Further, if a separate conductive member is provided for the nozzle, then it is possible to employ an inexpensive nozzle, such as a dispensable nozzle.

Any possible defective electrical connection need not be considered when the test tube or both the test tube and support stand are moved, thus ensuring the positive detection of the liquid level.

According to the present invention, unless the material of the container prevents the external detection of an electrostatic capacity in the container, various proper materials can be used, such as glass or plastics. The shapes of the container and electrodes can be changed or modified for the purpose of analysis intended.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a cross-sectional view showing a pair of plate-like electrodes and

FIG. 2B is a cross-sectional view showing a pair of curved plate-like electrodes;

FIG. 3A is a view showing a circuit created between a pair of electrodes when a nozzle is in contact with a liquid level as well as signal waveforms in the electrical circuit and FIG. 3B is a view showing a circuit created when the nozzle is in contact with the liquid level;

FIG. 4 is a schematic view generally showing an arrangement of a liquid level detector according to a second embodiment of the present invention.

DETAILED DESCRIPTION OF THE PREFERRED EMBODIMENTS

Figure 1:
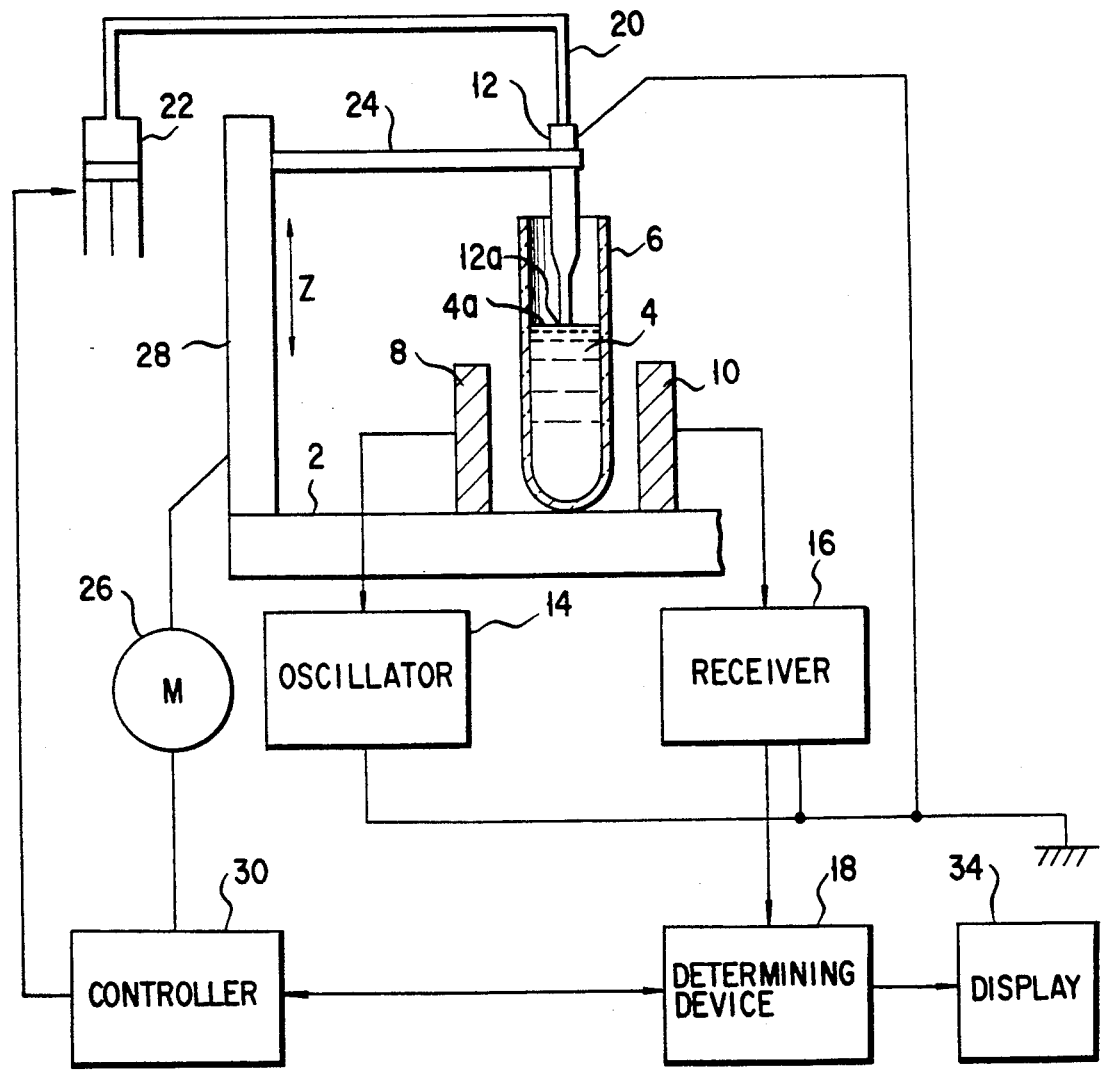
FIG. 1 is a schematic view generally showing an arrangement of a liquid level detector according to a first embodiment of the present invention.

FIG. 1 shows a first embodiment of the present invention.

A test tube 6 holding a liquid specimen 4, such as blood corpuscle and blood, therein is placed on a base plate 2 of nonconductive material such that it is set between first and second electrodes 8 and 10. A nozzle 12 of nonconductive material is inserted into the test tube 6 to take up the liquid specimen 4.

The electrodes 8 and 10 may be flat plate-like in cross-section as shown in FIG. 2A and curvilinear plate-like as shown in FIG. 2B.

In FIG. 1, the first and second electrodes 8 and 10 are electrically connected to an oscillator 14 and receiver 16, respectively. A nozzle 12 is electrically connected to a common zero potential level between the oscillator 14 and the receiver 16. The oscillator 14 generates a rectangular ware or a sine wave oscillation signal. The oscillation signal is supplied from the first electrode 8 via the test tube 6 and second electrode 10 to the receiver 16. The receiver 16 supplies a signal output corresponding to its received signal to a determining device 18 where, in accordance with the signal output of the receiver 16, determination is made as to whether or not a tip end 12a of the nozzle 12 is set in contact with a liquid level 4a of the specimen 4.

The detail of the determination will be explained below.

The liquid specimen 4 in the test tube 6 is taken up by the nozzle under the suction of a distributor 22 which is connected to the nozzle 12 through a tube 20. The nozzle 12 is supported by a vertically movable arm 24 which is moved, by a motor 26, in a vertical direction along a column 28 as indicated by an arrow Z. The motor 26 is controlled by a controller 30 on the basis of a control signal of the determining device 18.

The operation of a liquid level detector thus arranged will be explained below with reference to FIGS. 1 and 3A and 3B.

Let it first be assumed the the tip end 12a of the nozzle 12a is placed in an initial state, that is, not in contact with the liquid level 4a. In the initial state it follows that the tip end 12a of the nozzle is placed at a higher position than the liquid level 4a or there is no specimen 4 present in the test 6.

In the initial state, a circuit is created among the first electrode 8, test tube 6 and second electrode 10 in a way to be shown in FIG. 3A.

In this state, an electrostatic capacity C1 is created between the first electrode 8 and the test tube 6 and an electrostatic capacity C2 between the second electrode 10 and the test tube 6 and an electrostatic capacity C3 is created in the test tube 6. RL in FIG. 3A denotes a zero potential level whereby the electric signal from the first electrode 8 to the second electrode 10 is grounded.

Disregarding a resistance such as a connection line in the liquid level detector, an electric oscillation signal of the oscillator 14, for example, a sine wave signal P1, is subject to some loss only at these areas of C1, C3 and C2 and supplied, as a sine wave signal, to the receiver 16.

Now let it be assumed that the nozzle 12 is lowered from the initial state by driving the arm of a Z axis drive mechanism 24. If, in this case, the tip end 12a of the nozzle is brought into contact with the liquid level 4a of the liquid specimen, a common impedance Zs is created, by the nozzle 12, between the electrostatic capacities C1 and C2, as shown in FIG. 3B, instead of the electrostatic capacity C3. The energy of the rectangular signal P3 is decreased through the presence of the impedance Zs so that the rectangular wave signal P3 is received, by the receiver 16, at an amplitude level appreciably lower than that of the rectangular wave signal P2.

Alternatively, when a sine wave signal S1 is used as an oscillation signal of the oscillator 14, it is possible to obtain a change in level of those signals S2 and S3 as in the case of the change in level of the rectangular wave signals P2 and P3.

Unless there is a change in level of a received signal P2 or S2 in the initial state, the determining device 18 determines its received signal level as a reference signal level indicating that the nozzle is not brought into contact with the liquid level 4a and continues lowering the nozzle 12 under the control of the controller 30.

When the received signal varies in level as in the case of the received signal P3 or S3, the determining device determines based on the received signal level that the tip end of the nozzle 12 has been brought into contact with the liquid level 4a. As a result, the lowering of the nozzle 12 is stopped through the control of the controller 30.

Since, in the latter case, the specimen 4 is set at a zero potential level, it is possible to decrease the electrode-to-electrode electrostatic capacity to an extremely small extent and hence to make such a determination, by the determining device, with high accuracy.

The change in level of the electrostatic capacity resulting from the change in level of the received signal as in the case of FIGS. 3A and 3B can occur even if the nozzle 12 is made of a material of a low conductivity of the order of a few M$\Omega$. As the nozzle 12, use can be made of an inexpensive disposable nozzle made of a conductive synthetic resin, etc.

Further, since the pair of electrodes 8, 10 are arranged independently of the test tube 6, there is no limit on the material of which the test tube 6 is made. It is thus possible to use an inexpensive nonconductive test tube 6, such as glass or synthetic resin.

In the aforementioned determination, unless there is any specimen 4 present in the test tube 6, it will follow that, because there is no change in level of the signal received by the receiver 16, the nozzle 12 continues its downward movement. In order to prevent such an inconvenience, it is possible to impart, to the determining device, a function to determine the presence or absence of the specimen 4 in the test tube 6. If this is the case, then information indicating an amount of descent of the nozzle 12 from the initial position is fed to the device 18 by the controller 30. The determining device 18 compares the actual amount of descent of the nozzle 12 which is conveyed as data from the controller 30 with a limit descent level of the nozzle initially set and determines whether or not there is any specimen 4 present. That is, when the nozzle 12 is regarded as being not in contact with a specimen level 4a through the reception of a signal by the receiver 16 in spite of the fact that the amount of descent exceeds the limit descent level, the determining device determines that there is no specimen present. In this case, the descent of the nozzle 12 is stopped under the control of the controller 30 and information indicating "the absence of the specimen" is displayed on a proper display means, such as a display unit 34, thus alerting the operator to this state.

When it is determined based on the received signal of the receiver 16 that the nozzle 12 has been brought into contact with the surface level 4a of the liquid specimen, the descent of the nozzle 12 is stopped under the control of the controller 30, displaying information indicating "the presence of the specimen" on the display unit 34.

The result of determination by the determining device 18 can be utilized not only for the descent control of the nozzle 12 and presence or absence of the specimen 4 but also the suction of the liquid by the distributor 22. When it is determined by the determining device 18 that the tip end 12a of the nozzle 12 is lowered in contact with the liquid level 4a, the controller 30 imparts a suction operation start instruction to the distributor 22 so that the suction of the liquid specimen by the distributor 22 can be started based on the instruction.

FIG. 4 shows a second embodiment of the present invention. Since the basic structure and operation of the second embodiment are substantially the same as these of the first embodiment, an explanation will be restricted only to their difference. In the first embodiment, although the nozzle 12 serves also as a conductive member for detecting the liquid level 4a of the nozzle 12, use in made, in the second embodiment, of a conductive member provided separate from the nozzle 12.

Stated in more detail, a conductive rod-like member 32 is electrically connected, in place of the aforementioned conductive member 12, to a zero potential level common to an oscillator 14 and receiver 16. The rod-like member 32, together with a nozzle 12, is supported by the arm 24 so that it is vertically movable in interlock with the nozzle 12 with a forward end 32a of the member set flush with a tip end 12a of the nozzle 12.

In the case where the nozzle 12 and conductive rod-like member 32 are provided separate from each other, those signals as shown in FIGS. 3A and 3B can be detected even if the nozzle 12 is made of a non-conductive material and it is, therefore, possible to achieve the same object as set out in connection with that done in the first embodiment. Since the rod-like member 32 is only one, the diameter of a test tube 6 cannot be so restricted as in a conventional case where a pair of electrodes are employed. It is, therefore, possible to readily insert the rod-like member in the test tube 6.

Figure 5A:
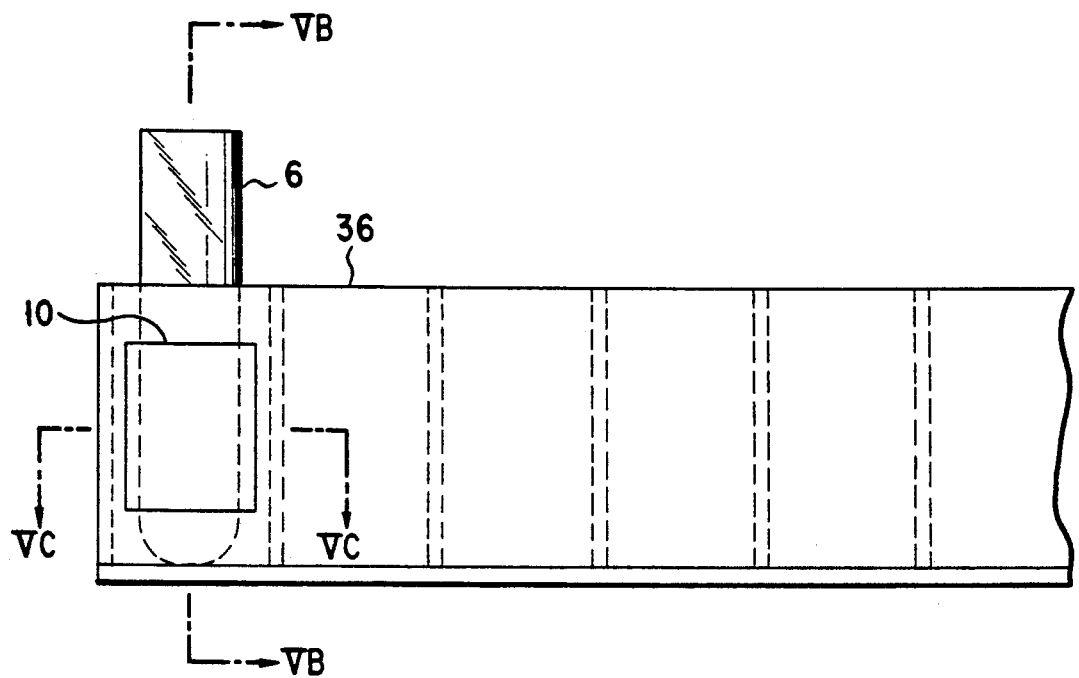
FIG. 5A is a view showing an arrangement showing a stand and electrodes in an apparatus according to a third embodiment of the present invention.
Figure 5B:
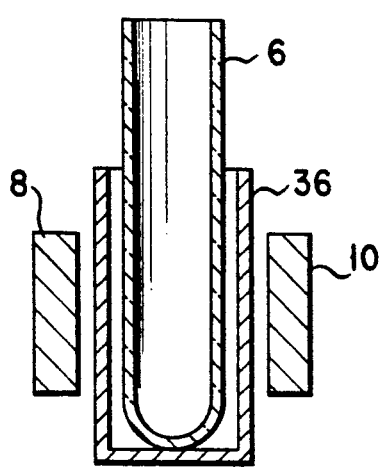
FIG. 5B is a cross-sectional view, as taken along line VB—VB in FIG. 5A.
Figure 5C:
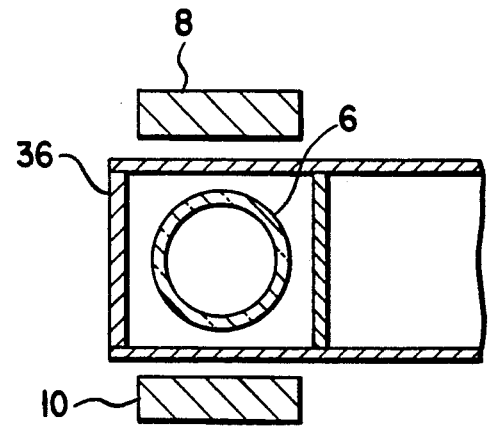
FIG. 5C is a cross-sectional view, taken along line VC—VC in FIG. 5A.

FIGS. 5A to 5C show a third embodiment of the present invention. An explanation of this embodiment is restricted only to a different aspect from those of the first and second embodiments, as will be set out below.

A liquid level detector of the third embodiment includes a support stand 36 for supporting a plurality of test tubes, one of which is shown in FIG. 5A for brevity's sake. A pair of electrodes 8, 10 are located relative to the stand 36 with each test tube between the electrodes 8 and 10. Even in this arrangement, it is possible to detect the level of a liquid as in the same way as set out in connection with the first and second embodiments of the present invention. Since, in this case, any proper material can be used for the stand 36 as in the case of the test tube 6, it is possible to employ an inexpensive material of which the stand is made.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for detecting a level of a liquid held in a container, comprising:
   taking means, vertically movable relative to the liquid level, for taking up the liquid;
   first and second electrodes arranged with the container set therebetween;
   generating means, electrically connected to the first electrode, for generating an electrical signal;
   receiving means, electrically connected to the second electrode, for receiving the electrical signal from the generating means through a route of the first electrode, container and second electrode;
   a conductive member, electrically connected to a zero potential level common to the generating means and receiving means, vertically movable relative to the liquid level such that the taking means and the conductive member are moved in unison;
   means for detecting a change of the received electrical signal with respect to a reference electrical signal which is received by the receiving means when the conductive member is not in contact with the liquid level and for determining that the conductive member is in contact with the liquid level, when there is the change of the received signal, so that the liquid level is detected and that the conductive member is not in contact with the liquid level when there is no change of the received signal; and
   means for controlling a vertical movement of the taking means relative to the liquid level based on the determination made by the detecting means.

2. The apparatus according to claim 1, wherein the conductive member is made of a conductive synthetic resin.

3. The apparatus according to claim 1, wherein the conductive member is formed as the taking means.

4. The apparatus according to claim 1, wherein a forward end of the conductive member is set flush with a forward end of the taking means.

5. The apparatus according to claim 4, wherein the taking means is made of a non-conductive material.